United States Patent [19]

Eian et al.

[11] Patent Number: 4,740,600

[45] Date of Patent: Apr. 26, 1988

[54] PHOTOLABILE BLOCKED SURFACTANTS AND COMPOSITIONS CONTAINING THE SAME

[75] Inventors: Gilbert L. Eian; John E. Trend, both of St. Paul, Minn.

[73] Assignee: Minnesota Mining and Manufacturing Company, St. Paul, Minn.

[21] Appl. No.: 816,250

[22] Filed: Jan. 6, 1986

Related U.S. Application Data

[62] Division of Ser. No. 608,954, May 10, 1984, Pat. No. 4,599,273, which is a division of Ser. No. 177,288, Aug. 11, 1980, Pat. No. 4,478,967.

[51] Int. Cl.$^4$ .................... C11C 11/00; C09F 5/00; C07F 125/06
[52] U.S. Cl. .................... 546/165; 430/253; 430/270; 522/65; 524/198; 524/199; 524/200; 560/157; 560/161; 560/163; 560/164; 560/165; 560/166; 560/167; 260/404
[58] Field of Search ............... 430/270, 253; 522/65; 524/198–200; 560/157, 163, 164, 165–167, 161; 546/165; 260/404

[56] References Cited

U.S. PATENT DOCUMENTS

| | | | |
|---|---|---|---|
| 3,060,023 | 10/1962 | Burg et al. | 96/29 |
| 3,133,902 | 5/1964 | Denchfield | 560/163 |
| 3,203,805 | 8/1965 | Burg et al. | 96/115 |
| 3,247,162 | 4/1966 | Newland et al. | 260/45.9 |
| 3,353,955 | 11/1967 | Colgrove | 96/28 |
| 3,436,402 | 4/1969 | Cassady et al. | 560/163 |
| 3,445,229 | 5/1969 | Webers | 96/28 |
| 3,469,982 | 9/1969 | Celeste | 96/35.1 |
| 3,591,377 | 7/1971 | Alsup | 96/35.1 |
| 3,607,264 | 9/1971 | Celeste et al. | 96/35.1 |
| 3,745,188 | 7/1973 | Bottorff | 260/456 R |
| 3,770,438 | 11/1973 | Celeste | 96/67 |
| 3,840,579 | 10/1974 | Fan | 260/456 R |
| 3,849,137 | 11/1974 | Barzynski et al. | 96/67 |
| 3,877,941 | 4/1975 | Lohmann | 560/163 |
| 3,926,636 | 12/1975 | Barzynski et al. | 522/174 |
| 3,954,826 | 5/1976 | Sugimoto et al. | 260/456 R |
| 3,997,349 | 12/1976 | Sanders | 96/75 |
| 4,050,936 | 9/1977 | Takeda et al. | 96/35.1 |
| 4,075,175 | 2/1978 | Foss | 260/67 R |
| 4,086,210 | 4/1978 | Petropoulos | 260/67 R |
| 4,155,892 | 5/1979 | Emmons et al. | 524/591 |
| 4,205,989 | 6/1980 | Moriya et al. | 430/306 |
| 4,287,255 | 9/1981 | Wong et al. | 428/343 |
| 4,288,479 | 9/1981 | Brack | 428/40 |
| 4,369,244 | 1/1983 | Eian et al. | 430/306 |
| 4,467,022 | 8/1984 | Eian et al. | 430/259 |
| 4,478,967 | 10/1984 | Eian et al. | 524/87 |
| 4,511,641 | 4/1985 | Busman et al. | 430/259 |
| 4,511,730 | 4/1985 | Fields | 560/165 |
| 4,554,238 | 11/1985 | Bushman | 430/258 |
| 4,599,273 | 7/1986 | Eian et al. | 524/239 |

FOREIGN PATENT DOCUMENTS

| | | | |
|---|---|---|---|
| 629495 | 1/1963 | France | 260/456 |
| 655612 | 11/1964 | France | 260/456 |
| 8102261 | 8/1981 | PCT Int'l Appl. | 428/345 |
| 968848 | 9/1964 | United Kingdom | 524/259 |

OTHER PUBLICATIONS

Inou et al., *Nippon Shashin Gakkai-Shi*, vol. 41, No. 4, pp. 245–249 (1978); Homma et al., pp. 250–253.
Komoto and Co. Ltd., Tokio (German Pat. No. 2,716,422).
Berkower et al., *Photographic Science and Engineering*, vol. 12, No. 6, Nov.–Dec. pp. 283–287 (1967).
Nakayama et al., *Society of Photographic Scientists and Engineers*, vol. 22, No. 3, pp. 138–141, May–Jun. (1978).
Amit et al., *Photosensitive Protecting Groups*, Israel J. of Chem. 12 (1–2), 103–113 (1974).
Woodruff et al., *Photographic Science and Engineering*, vol. 11, No. 2, pp. 93–97; Mar.–Apr. (1967).
Chem. Abs. 79-42074, Babayan et al. (1973).
Rosen, "*Surfactants & Interfaced Phenomena*", 1978, Wiley & Son, pp. 83–86.
Rajasekharan *Photoremovable Protecting Group in Organic Synthesis*, 1980 (1) 1–26 Synthesis.

*Primary Examiner*—Herbert J. Lilling
*Attorney, Agent, or Firm*—Donald M. Sell; James A. Smith; Richard Francis

[57] ABSTRACT

Surfactants which are blocked against surfactant action (identified herein as "photolabile blocked surfactants") by a photolabile protective or masking group but which, on exposure to actinic radiation, become unblocked are provided. Coating compositions in which surfactant is formed on irradiation are provided by blending the photolabile blocked surfactant with polymeric film-forming materials.

Compositions containing the photolabile blocked surfactants are useful when employed as protective coatings on various substrates or as the adhesive in a pressure sensitive adhesive tape. Although initially well adhering to a substrate, such compositions may be readily removed from the substrate following exposure of the same to suitable radiation which unblocks the surfactant to permit it to regain its surfactant activity.

2 Claims, No Drawings

PHOTOLABILE BLOCKED SURFACTANTS AND COMPOSITIONS CONTAINING THE SAME

This is a division of application Ser. No. 608,954 filed May 10, 1984, now U.S. Pat. No. 4,599,273 which is a division of application Ser. No. 177,288, filed Aug. 11, 1980, now U.S. Pat. No. 4,478,967.

TECHNICAL FIELD

This invention relates to surfactants which are blocked against surfactant activity and which are capable of regaining surfactant activity upon exposure to actinic radiation, to coating compositions containing the same, and to substrates coated with such compositions.

BACKGROUND ART

Many articles in the chemical literature discuss the use of photolabile groups to block (specifically to protect) a particular functional group, such as the carboxylic acid group, e.g., during synthesis involving polyfunctional molecules. In a review entitled *Photosensitive Protecting Groups*, Amit et al, Israel J. of Chem. 12 (1–2), 103–113 (1974) discuss the chemistry of photolabile protecting groups for carboxylic acids and give a large list of supporting references. None of these references, however, teach the blocking of surfactants by photolabile groups.

Coating compositions suitable for providing substrates such as polished sheet material, machinery, molded articles and the like with a protective film or coating that can be cleanly and inexpensively removed have been investigated for many years. Much of this investigation has been directed to adhesives for uses on tapes or papers that can be applied to the substrate and peeled off cleanly when desired. These tapes and papers generally tend to age with time so that, when removed, adhesive residues likely will remain on the surface of the substrate. Such tapes and papers are many times also unsatisfactory for use on substrates other than flat surfaces. Protective compositions which can be applied by brush, spraying or the like and removed when desired by a solvent, preferably water, have also been described. The use of such compositions for protection of substrates is less desirable because of untidy, often hazardous and corrosive conditions arising from the use of solvents to remove the coating.

DISCLOSURE OF INVENTION

The present invention provides novel photolabile blocked surfactants, compositions comprising the photolabile blocked surfactants, e.g., a coating composition in which surfactant is formed upon exposure to suitable radiation, and substrates bearing coatings of such compositions. The novel photolabile blocked surfactants of the invention are surfactants (i.e., compounds characterized by having a hydrophobic group and at least one polar hydrophilic group) having their polar group(s) masked by a covalently bonded photolabile masking group. Because of the photolabile mask, the masked surfactant has substantially reduced surfactant activity as compared to the same surfactant in the unmasked state and, on exposure to suitable radiation, the mask is removed, substantially restoring the surfactant to its original surface activity.

Specifically, the photolabile surfactant compounds of the invention have the general formula $(P-X)_a R$ wherein $(-X)_a R$ is the hydrogen-eliminated residue of a surfactant having the formula $(H-X)_a R$ including the polar divalent radical X, P is a covalently bonded photolabile masking group which prior to exposure to actinic radiation masks the polar properties of X and upon exposure to actinic radiation will unmask the polar properties of X, and R is a hydrophobic group which provides in the surfactant $(H-X)_a R$ a log (critical micelle concentration, hereinafter designated "CMC") equal to or less than $-2$ and "a" is a number from 1 to 4 to satisfy the valency of R.

The coating composition comprises an actinic radiation-transmissive film-forming binder which has blended therein a photolabile blocked surfactant compound having the general formula $(P-X)_a R$, as defined above, in a quantity, functionally stated, sufficient to cause an appreciable change in the surface characteristics of the coating composition, i.e., a change in wettability or adhesion, upon exposure to actinic radiation. A preferred embodiment of the composition is of use in coatings which upon radiation are made releasable from the substrate.

A simple infrared spectroscopic analysis technique may be employed to identify the suitable photolabile covalently bonded blocked surfactants of the present invention. In this technique, a small amount (e.g., about 10–100 mg) of the test photolabile blocked surfactant (as a thin liquid film or as a mull in mineral oil) is analyzed to obtain an infrared spectrum. The sample is thereafter exposed to an ultraviolet source (e.g., using an H3T7 lamp from a distance of 3 cm) for a brief length of time and a second IR spectrum is obtained of the UV exposed sample. Useful compounds will show a change in the infrared spectrum due to breaking of the covalent bond and liberation of the polar group of the unblocked surfactant after UV light exposure. The UV light exposure time needed to cause this change will generally depend on several factors including the photosensitivity of the test compound, film thickness, etc. Generally, exposures of from 5 to 50 minutes will be sufficient and 15–30 minute exposures are more common.

Coated substrates according to the invention are provided by any of a variety of substrates coated with the coating composition described above.

BEST MODE FOR CARRYING OUT THE INVENTION

The surfactants constituting the novel photolabile blocked surfactants of the invention are those surfactants which, in their salt form, are commonly known as ionic surfactants. Suitable ionic surfactants are those having one or more salt forming polar group including carboxylic, sulfonic, phosphonic, phosphinic, sulfinic, amino and the like polar groups.

Suitable photolabile masking groups for use in the photolabile blocked surfactants (sometimes referred to as photoactivatable release agents) of the invention are any of the photolabile masking groups (often termed protecting groups) recognized in organic chemistry, particularly the chemistry of aminoacids, that can be covalently bonded to the polar groups (see previously cited review). Examples of such protecting groups include 2-nitrobenzyl, phenacyl, 2-nitroanilino, 2,4-dinitrobenzenesulfenyl, 2-(2-azidoaryl)ethyl, 7-nitroindolino, β-nitrocinnamyl, and 8-nitrotetrahydroquinolino groups that can be substituted by one or more auxochromic or bathochromic groups.

Preferred photolabile blocked surfactants of the invention include those of the formula $(P-X)_a R$ wherein P is as defined above; and
X is a polar group selected from

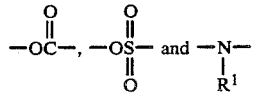

wherein $R^1$ is selected from hydrogen and lower alkyl having one to four carbon atoms;
R is selected from:

$R^2-$ (a)

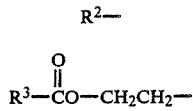 (b)

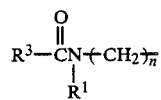 (c)

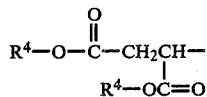 (d)

wherein $R^2$ is
(1) straight chain alkyl, alkenyl, alkynyl, or alkylphenyl group having 12 to 30 carbon atoms when X is

(2) straight chain alky, alkenyl, alkynyl, or alkylphenyl group having 15 to 30 carbon atoms when X is

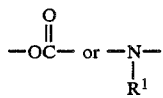

in which $R^1$ is defined above; or
(3) a perfluoroalkyl -alkenyl, or -alkynyl group having 7 to 30 carbon atoms;
$R^3$ is a straight chain alkyl, alkenyl, alkynyl, or alkylphenyl group having 11 to 30 carbon atoms or a perfluoroalkyl group having 7 to 30 carbon atoms;
$R^4$ is a straight chain alkyl, alkenyl, alkynyl, or alkylphenyl or perfluoroalkyl -alkenyl, or -alkynyl group having 7 to 30 carbon atoms;
n is 1 or 2; and
a is 1.

The most preferred photolabile blocked surfactants of the invention have the general formulae:

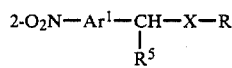 IIa

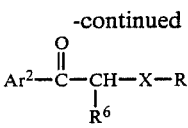 IIb

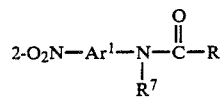 IIc

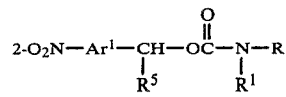 IId

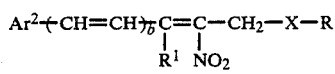 IIe wherein X, R and $R^1$ are as defined above;
$Ar^1$ is a mononuclear or polynuclear divalent aryl group having 6 to 14 carbon atoms or heteroaromatic group having 5 to 13 carbon atoms with heteroatoms selected from oxygen, nitrogen or sulfur atoms, the nuclei of which may be substituted by one or more auxochromic or bathochromic groups, examples of which include nitro, chloro, bromo, phenyl, lower alkyl, lower alkoxy, lower thioalkoxy, amino, lower alkyl or dialkylamino, and the like groups and the aryl group $Ar^1$ may be the aryl group in a polymer; $Ar^2$ is preferably the same as $Ar^1$ except that $Ar^2$ is monovalent;

$R^5$ is preferably hydrogen but may be lower alkyl or phenyl which may also be substituted by an auxochromic or bathochromic group as defined for $Ar^1$ or a lower alkylene group joining CH to $Ar^1$ and forming a five- or six-membered heterocyclic ring;

$R^6$ is preferably phenyl substituted by 3-alkoxy or 3,5-dialkoxy in which the alkyl group has 1 to 4 carbon atoms but can be a hydrogen atom, a lower alkyl group, e.g., having from 1–4 carbon atoms, or a phenyl group;

$R^7$ can be hydrogen but preferably is lower alkyl having 1 to 4 carbon atoms or most preferably is lower alkylene having 2 to 4 carbon atoms joining N to $Ar^1$ forming five- or six-membered heterocyclic ring; and
b is zero or one.

Examples of specific preferred photolabile blocked surfactants of the invention include:

IIa Compounds

2-Nitrobenzyl tetradecanesulfonate
2-Nitrobenzyl hexadecanesulfonate
2-Nitrobenzyl heptadecanoate
2-Nitrobenzyl hexadecanoate
4,5-Dimethoxy-2-nitrobenzyl octadecanoate
2-Nitrobenzyl 9-octadecenoate
2-Nitrobenzyl octadecanoate
2-Nitrobenzyl 4-dodecylbenzenesulfonate
4,5-Dimethoxy-2-nitrobenzyl hexadecanoate
4,5-Methylenedioxy-2-nitrobenzyl perfluorooctanoate
4,5-Methylenedioxy-2-nitrobenzyl bis(2-ethylhexyl)sulfosuccinate
4-Dimethylamino-2-nitrobenzyl N-octadecanoylsarcosinate
2,4-Dinitrobenzyl N-("cocoyl")taurate
3,4,5-Trimethoxy-2-nitrobenzyl hexadecanesulfonate
4,5-Dimethoxy-2-nitrobenzyl perfluorooctanoate
2-Nitrobenzyl N-octadecanoylsarcosinate
2-Nitrobenzyl tetraeicosanoate 2-Nitrobenzyl perfluorooctanoate
4,5-Dimethoxy-2-nitrobenzyl hexadecanesulfonate
N-(2-Nitrobenzyl)perfluorooctylamine
N-(2-Nitrobenzyl)octadecylamine
1-Nitronaphth-2-ylmethyl perfluorooctanoate
10-Nitro-1,2,3,4-tetrahydronaphth-1-yl perfluorooctanoate
7-Nitroindan-1-yl perfluorooctanoate
4-Dimethylamino-2-nitrobenzyl perfluorooctanoate
N-Methyl-(2-nitrobenzyl) octadecylamine
2-Octadecanoylpropanoyl substituted polystyrene
2-Perfluorooctanoylacetyl substituted poly(styrene/butadiene)
Bis(2-Nitrobenzyl ester) of 9-octadecenoic acid dimer IIb Compounds 3'-Methoxybenzoin octadecanoate
3',5'-Dimethoxybenzoin perfluorooctanoate
3'-Methoxybenzoin hexadecanoate
3'-Methoxybenzoin perfluorooctanoate
α-Methylphenacyl tetradecanesulfonate
α-Methylphenacyl perfluorooctanoate
α-Methylphenacyl hexadecanesulfonate
α-Methyl-4-nitrophenacyl perfluorooctanoate
α-Phenylphenacyl N-(ocatadecanoyl)taurate
α-Phenylphenacyl pentadecylbenzenesulfonate
α-(2,4-Dichlorophenyl)phenacyl bis(2-ethylhexyl)sulfosuccinate Phenacyl octadecanoate
α-Methylphenacyl 14,14,14-trifluorohexadecanesulfonate
α-Phenylphenacyl 1,1-difluorooctadecanoate
α-n-Butylphenacyl octadecanoate
N-[α-(3-Methoxyphenyl)-4-chlorophenacyl]octadecenylamine
1-Indanon-2yl perfluorooctanoate
3,4-Dihydro-1(2H)-naphthalenon-2-yl perfluorooctanoate
3'-Methoxybenzoin hexadecanesulfonate IIc Compounds N-Perfluorooctanoyl-2-nitroaniline
N-Perfluorooctanoyl-N-methyl-2-nitroaniline
N-Octadecanoyl-2-nitroaniline
1-Perfluorooctanoyl-8-nitro-1,2,3,4-tetrahydroquinoline
N-Octadecanoyl-8-nitro-1,2,3,4-tetrahydroquinoline IId Compounds N-Perfluorooctyl-O-(2-nitrobenzyl)carbamate
N-Octadecyl-O-(2-nitrobenzyl)carbamate
N-Perfluorooctyl-O-(2-nitro-4-methoxybenzyl)carbamate
N-Octadecyl-O-(4,5-dimethoxyl-2-nitrobenzyl)carbamate IIe Compounds β-Nitrocinnamyl tetradecanesulfonate
β-Nitrocinnamyl octadecanoate
β-Nitrocinnamyl perfluorooctanoate
4-Methoxy-β-Nitrocinnamyl octadecanoate
5-Phenyl-2-nitro-1-octadecanoyloxypenta-2,4-diene The compounds of general Formulae IIa, IIb, and IIe where X is

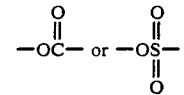

are prepared from the corresponding alcohol or halide and surfactant carboxylic or sulfonic acid or preferably acid chloride by conventional esterification procedures such as are described by Bottorff, U.S. Pat. No. 3,745,188; Barltrop et al, *Chemical Communications*, 882 (1966); and Sheehan et al, J. Am. Chem. Soc. 86; 5277 (1964) and J. Org. Chem. 38 (21), 3771 (1973).

The compounds of general Formulae IIa and IIb where X is

are prepared from the corresponding halide and surfactant amine in accordance with well known alkylation procedures. A preferred method for preparing the compounds of Formula IIa is to condense a nitrobenzaldehyde with a surfactant amine and reduce or reductively alkylate the Schiff's base obtained in accordance with well known methods to the desired blocked surfactant. The photosensitive 2-nitroarylamine amides of Formula IIc are prepared by acylation of o-nitroarylamines with surfactant carboxylic acid chlorides. The photosensitive carbamates of Formula IId are prepared by conventional urethane reaction of the corresponding nitrobenzyl alcohol and a hydrophobic group-containing isocyanate such as perfluorooctylisocyanate, perfluorododecylisocyanate, hexadecylisocyanate, octadecylisocyanate and pentadecylphenylisocyanate.

Exemplary 2-nitrobenzyl alcohols of use for preparing photo-activatable surfactants of Formulae IIa and IId include 2-nitrobenzyl, 2,4-dinitrobenzyl, 1-nitronaphthylmethyl, 4,5-dimethoxy-2-nitrobenzyl, 4,5-methylenedioxy-2-nitrobenzyl, 4-dimethylamino-2-nitrobenzyl, 4,5-dimethyl-2-nitrobenzyl, 4,5-dichloro-2-nitrobenzyl, 4-bromo-2-nitrobenzyl, 4-phenyl-2-nitrobenzyl, 4-methylthio-2-nitrobenzyl, 2-nitro-α-phenylbenzyl, bis(2-nitrophenyl)methyl, 2-nitro-α-methylbenzyl, 2-nitro-α-n-butylbenzyl alcohol and the like. The corresponding chloride, bromide, and aldehydes of the aforenamed alcohols are suitable for the preparation of the compounds of Formula IIa wherein X is

The corresponding chlorides and bromides are also useful for preparation of the compounds of Formula IIa wherein X is

Exemplary phenacyl alcohols of use for preparing the blocked photoactivatable surfactant of Formula IIb include benzoin, α-methylphenacyl alcohol, 3'-methoxybenzoin, and 3',5'-dimethoxybenzoin and the corresponding halides.

Exemplary nitroarylamines of use for preparing the blocked photoactivatable surfactants of Formula IIc include 2-nitroaniline, N-methyl-2-nitroaniline, 8-nitro-1,2,3,4-tetrahydroquinoline, 4-chloro-2-nitroaniline, and 4-methoxy-2-nitroaniline.

Exemplary cinnamyl alcohols of use for preparing compounds of Formula IIe include β-nitrocinnamyl alcohol, 4-methoxy-β-nitrocinnamyl alcohol and 5-phenyl-2-nitropenta-2,4-dien-1-ol.

The film-forming binder component of the radiation activatable compositions of the invention are thermoplastic organic polymers preferably having a molecular weight of at least 10,000. Suitable polymers include: (a) copolyesters based on terephthalic, isophthalic, sebacic, adipic and hexahydrophthalic acids such polyesters are sold under the trade designation "Vitel" by the Goodyear Tire and Rubber Company, (b) alkyd resins based on phthalic anhydride and glycerine available from Enterprise Paint Company under the trade designation "EPIC" Varnish, (c) polyamides such as poly(hexamethyleneadipamide) and polycaprolactam, (d) vinyl acetate polymers such as that available under the trade designation "VINAC" ASB516 from Air Products Company and vinyl chloride copolymers such as the copolymer with vinyl acetate, e.g., those sold under the trade designation "VMCH", "VAGH", or "VYHH" by the Union Carbide Company and under the trade designation "Geon" resin by the B.F. Goodrich Company, (e) vinylidene chloride copolymers, (f) ethylene copolymers, e.g., ethylene or propylene and vinyl acetate, (g) polyacrylates such as polymethyl methacrylate and the copolymers of acrylic acid esters with other ethylenically unsaturated monomers, e.g., that sold under the trade designation "Carboset 525" by the B.F. Goodrich Company and methacrylate resins such as that sold under the trade designation "Elvacite" by the DuPont Company, the pressure sensitive adhesive copolymers of "soft" acrylic esters such as butyl or isooctyl acrylate and a "hard" monomer such as acrylic acid or acrylamide, (h) cellulose esters such as cellulose acetate/butyrate, (i) polyvinyl acetals such as polyvinyl butyral, (j) polyurethanes such as that sold by B.F. Goodrich Company under the trade designation "Estane 5715", (k) the polycarbonates, and (l) styrene-maleic anhydride or maleic acid copolymers.

The radiation-releasable coating compositions of the invention may be prepared by mixing by any convenient method the film-forming binder and photolabile surfactant in a suitable solvent. Generally, from about one to about ten parts, preferably about two to five parts of photolabile surfactant are used per 100 parts of film-forming binder. Solutions are prepared to contain about 10 to 50 weight percent concentration of solids, the concentration used being that which provides a solution having a viscosity most suitable to the method by which the composition is to be applied to the substrate.

Solvents for use in the coating composition are chosen on the basis of film-forming binder. Suitable solvents include ketones such as acetone, methylethylketone, and methylisobutyl ketone; aromatic hydrocarbons such as benzene and toluene; halocarbons such as chloroform, methylene chloride, and trichloroethylene; esters such as ethyl acetate and propyl butyrate; ethers such as diethyl ether, dioxane, and tetrahydrofuran; nitromethane; nitroethane; and acetonitrile.

Various additives, such as coating aids, wetting agents, plasticizers, ultraviolet absorbers and dyes (as long as they do not absorb in the wavelength range of the photolabile release agent) can be added to the composition in amounts and for purposes that are well known. Particulate material such as pigments, e.g., carbon black, clays titanium dioxide, umber, ochre and the like, microfibers, glass microspheres, alumina, etc., may also be added; however, only small amounts, i.e., less than about 5%, can be tolerated since the surfactant liberated on irradiation will tend to orient about particulate material and be lost to orientation at the substrate surface.

The compositions are favorably used to provide substrates with a removable protective coating. Substrates that can be coated include metal, e.g., steel, nickel, aluminum; plastics, e.g., polyester, polyvinyl chloride, polyurethane, epoxy resins, phenol-formaldehyde resins, etc.; glass, ceramic and the like. The use of many primers on substrates to improve adherence of the coating is not detrimental since the protective coatings of the invention are releasable on irradiation even when applied over primers.

The substrate can be coated by any of the conventional means, including spray, brush, dip pad, roll-coating, curtain and knife techniques, and may, if desired, be dried under ambient or even conditions to provide coating films on the substrate.

A typical example of the use of the removable protective coatings of the invention is the use of the coating to protect a substrate against damage by abrasion during conditions such as shipment or a shaping operation, e.g., cutting. A composition of the invention is prepared, the substrate coated, and the coating dried. After the shipment or shaping operation, when it is desired to remove the protective coating, it is subjected to radiation having wavelengths preferably in the range between about 200 and 400 nanometers. Radiation having wavelengths above 400 nm can also be used when the protective coating contains photolabile blocked surfactants having auxochromic groups that extend the absorption characteristics of the blocked surfactant into the visible range of radiation. Protective coatings having photolabile blocked surfactants absorbing in the visible range are less desirable unless the protected substrate is to be manipulated in darkness since such coatings would have the tendency to release prematurely.

Suitable sources of radiation include carbon arcs, mercury vapor arcs, fluorescent lamps with ultraviolet radiation-emitting phosphors, argon and xenon glow lamps, and electronic flash units. Customarily, mercury-vapor arcs are used at a distance of 1 to 20 inches (2.5 to 50 cm) or more from the protective coating to bring about release. Radiation fluxes of 10 to 10,000 w/cm$^2$ are generally suitable for use.

The following examples will aid in further explaining, but should not be deemed as limiting, the instant invention. In all cases, unless otherwise noted, all parts and percentages are by weight.

PREPARATION OF PHOTOLABILE BLOCKED SURFACTANTS

Each of the photolabile blocked surfactants described herein is identified by a "Compound Number" which is used hereinafter to refer to the same.

EXAMPLE 1

2-Nitrobenzyl perfluorooctanoate (Compound 1)

Perfluorooctanoyl chloride (21.6 g, 0.05 mol) was added slowly with stirring to a solution of 2-nitrobenzyl alcohol (7.65 g, 0.05 mol) and triethylamine (5.2 g, 0.05 mol) in 100 ml benzene. During the addition, the temperature was allowed to rise to 50° C. and the triethylamine hydrochloride began to precipitate. After the addition was complete, the reaction was stirred an additional 30 minutes. The reaction was filtered and the filtrate evaporated in vacuo to give an oil which crystallized on cooling in an ice bath (m.p. 34°–35° C.). Benzene washings of the material retained on the filter paper gave a second fraction of oil which crystallized on cooling. Total yield was 11.97 g.

EXAMPLE 2

α-Methylphenacyl perfluorooctanoate (Compound 2)

2-Bromopropiophenone (10.65 g, 0.05 mol) was added to a solution of perfluorooctanoic acid (20.7 g, 0.05 mol) and triethylamine (5.05 g, 0.05 mol) in 100 ml of DMF. The solution was stored at 0°–2° C. for three days, filtered to remove precipitated ammonium salt, and mixed with 700 ml of ice water. The oil which separated was collected and crystallized from 95% ethanol to yield 6.2 g of the ester [IR 1775 cm$^{-1}$; UV (ethanol) $\lambda$max 244, 279 and 325 (sh) (nm)].

EXAMPLE 3

N-(2-Nitrobenzyl)octadecylamine (Compound 3)

Octadecylamine (13.5 g, 0.05 mol) was dissolved in warm absolute ethanol (300 ml) and 2-nitrobenzyl chloride was added. After three days at room temperature, the mixture was cooled and the unreacted octadecylamine which crystallized was removed by filtration. The filtrate was evaporated to dryness and the residue dissolved in dilute aqueous hydrochloric acid. Ether extraction of the acidic solution removed unreacted 2-nitrobenzyl chloride. The aqueous layer was made basic with potassium hydroxide solution and the resulting mixture was extracted with ether. The dried ether layer was evaporated to yield an oil which crystallized. Crystallization from methanol gave pure product (0.8 g, m.p. 53°–56° C.).

EXAMPLE 4

2-Nitrobenzyl octadecanoate (Compound 4)

In 100 ml benzene were mixed 2-nitrobenzyl alcohol (7.65 g, 0.05 mol) and triethylamine (5.06 g, 0.05 mol). To the solution octadecanoyl chloride (15.14 g, 0.05 mol) was added dropwise with stirring. The mixture was stirred an additional one hour and the precipitated triethyl amine hydrochloride was removed by filtration. The filtrate was evaporated to dryness and the residue crystallized from ethanol (yield 13.0 g, m.p. 60°–61° C.). The tetradecanoate (m.p. 46° C.) (Compound 5), hexadecanoate (m.p. 54° C.) (Compound 6), heptadecanoate (m.p. 48° C.) (Compound 7), and 9-octadecenoate (Compound 8) esters of 2-nitrobenzyl alcohol were similarly prepared using corresponding acyl chlorides in place of octadecanoyl chloride.

EXAMPLE 5

A. 2-Nitrobenzyl hexadecanesulfonate (Compound 9)

To a stirred solution of 7.65 g (0.05 mol) of 2-nitrobenzyl alcohol in 75 ml of benzene containing 5.05 g (0.05 mol) of triethylamine was added 16.25 g (0.05 mol of hexadecanesulfonyl chloride. The mixture was stirred an additional four hours. The mixture was evaporated to dryness in vacuo and the solid taken up into a mixture of ether and water. The ether layer was separated and dried over MgSO$_4$. Evaporation of the ether gave a solid which was crystallized from absolute ethanol (yield 14.3 g, m.p. 63°–65° C.).

B. 4,5-Dimethoxy-2-nitrobenzyl hexadecanesulfonate (Compound 10)

To a solution of 5.33 g (0.025 mol) of 4,5-dimethoxy-2-nitrobenzyl alcohol and 8.15 g (0.025 mol) hexadecanesulfonyl chloride in 100 ml of acetone, dicyclohexylamine (5 ml, slight excess) was added via motor driven syringe over 30 minutes. After the addition was complete, the reaction was stirred an additional 30 minutes. The precipitated dicyclohexylamine hydrochloride was removed by filtration and the acetone filtrate reduced in volume in vacuo until most of the product had precipitated (yield 9.5 g, m.p. 81°–82° C.).

EXAMPLE 6

A. 2-Bromopropionyl substituted polystyrene (Compound 11)

Polystyrene (20 g Dow Styron 678, general purpose) was dissolved in 200 ml of methylene chloride followed by 4.58 g (0.025 mol) 2-bromopropionyl chloride. Aluminum chloride (3.65 g, 0.0275 mol) was added portionwise with stirring over 20 minutes at room temperature. The mixture was poured into 600 ml of water containing 25 ml concentrated HCl. The phases were mixed until the methylene chloride became colorless; whereupon the methylene chloride layer was separated and poured slowly in methanol to precipitate the polymeric product, which was redissolved in methylene chloride then reprecipitated in methanol, collected and dried to give 14.5 g of functionalized polymer (% C=86.1, H=7.1%, Br=6.2%; approximately 9–10% of the rings are brominated).

B. 2-Octadecanoylpropanoyl substituted polystyrene (Compound 12)

A 6 g portion of 2-bromopropionyl substituted polystyrene (0.0047 mol Br) was dissolved in 30 ml of methylene chloride. Sodium octadecanoate (0.0047 mol) and DMF (30 ml) was added and the reaction was shaken at room temperature for ten weeks. Infrared spectral data indicated that ester groups had formed. The reaction mixture was poured into methanol and the precipitated polymer was redissolved (CH$_2$Cl$_2$) and precipitated (MeOH) (IR—1748 cm$^{-1}$, 1695 cm$^{-1}$).

EXAMPLE 7

3'-Methoxybenzoin octadecanoate (Compound 13)

3'-Methoxybenzoin (5 g, 0.021 mol) was dissolved in 200 ml of toluene containing one equivalent of triethylamine. One equivalent of octadecanoyl chloride in 20 ml of toluene was added slowly to the cooled (ice bath) stirred benzoin solution. Stirring was continued with ice bath cooling for one hour. The reaction mixture was then filtered free of precipitated amine salt and the filtrate was evaporated to give an oil which solidified to give a low melting solid. The hexadecanesulfonate (Compound 14) and perfluorooctanoate (Compound 15) (m.p. 55°-58° C.) esters were similarly prepared from the corresponding acid chlorides.

EXAMPLE 8

4,5-Dimethoxy-2-nitrobenzyl octadecanoate (Compound 16)

To a stirred mixture of 4,5-dimethoxy-2-nitrobenzyl alcohol (2.13 g, 0.01 mol) and 1.4 ml of triethylamine in 75 ml of methylene chloride at 5° C., octadecanoyl chloride (3.33 g, 0.01 mol) was added dropwise over 1.5 hours. The mixture was stirred overnight at room temperature. The homogeneous solution which was obtained was washed with saturated $NaHCO_3$ followed by water. The methylene chloride layer was dried over $Na_2SO_4$ and evaporated in vacuo to give a solid which was crystallized from ether-hexane to give 2.5 g of ester (m.p. 87°-89° C.).

EXAMPLE 9

4,5-Dimethoxy-2-nitrobenzyl perfluorooctanoate (Compound 17)

In 100 ml of toluene 4,5-dimethoxy-2-nitrobenzyl alcohol (2.13 g, 0.01 mol) and 1.4 ml of triethylamine were mixed. Perfluorooctanoyl chloride (4.33 g, 0.01 mol) was added dropwise to the stirred toluene solution. The reaction mixture was stirred an additional 30 minutes after the completion of the addition and then extracted with saturated $NaHCO_3$ and then water. The organic layer was dried over $Na_2SO_4$ and evaporated in vacuo to give an oil which solidified on overnight storage at 0°-2° C. The solid was crystallized from ether-hexane (m.p. 65°-66°), 4,5-Methylenedioxy-2-nitrobenzyl perfluorooctanoate (Compound 18) was similarly prepared from 4,5-methylenedioxy-2-nitrobenzyl alcohol (m.p. 70°-71° C.).

EXAMPLE 10

N-Octadecyl-O-(2-nitrobenzyl)carbamate (Compound 19)

A mixture of 7.7 g (0.03 mol) of octadecylisocyanate and 4.6 g (0.03 mol) 2-nitrobenzyl alcohol in 100 ml of toluene was refluxed for five days. On cooling, a solid precipitated which was filtered and washed with toluene to give 8.0 g (m.p. 84°-85° C.) of the carbamate.

EXAMPLE 11

Bis(2-Nitrobenzyl ester) of 9-octadecenoic acid dimer (EMPOL 1010) (Compound 20)

The bis acid chloride of 9-octadecenoic acid dimer was prepared from the acid dimer ("EMPOL" 1010[1])* with thionyl chloride in toluene. To a solution of 15.3 g (0.1 mol) 2-nitrobenzyl alcohol and 10.1 g (0.1 mol) triethylamine in 100 ml of benzene was added slowly under $N_2$ 30.0 g (0.05 mol) of the acid chloride with stirring. The reaction was stirred one hour at room temperature after the addition had been complete. The precipitated triethyl ammonium chloride was removed by filtration and the filtrate evaporated to dryness to give the diester.

*Footnotes 1-10 are identified following Example 80.

EXAMPLE 12

N-Octadecanoyl-8-nitro-1,2,3,4-tetrahydroquinoline (Compound 21)

8-Nitro-1,2,3,4-tetrahydroquinoline (1.8 g, 0.01 mol) was refluxed in 200 ml xylene with excess octadecanoyl chloride for ten days. The solvent was then evaporated in vacuo and the residue which remained was dissolved in ethanol. The ethanol was then evaporated in vacuo and the ethyl octadecanoate formed from the excess acid chloride was taken up in cold hexane and the product was isolated by filtration and crystallized from hexane (2.5 g, m.p. 61° C.).

PHOTOLABILE BLOCKED SURFACTANT COMPOSITIONS EXAMPLES 13-16

A series of coating solutions were prepared in methylethylketone to contain 30% by weight of "Carboset" 525[2.] (a carboxy functionalized acrylic resin available from B.F. Goodrich Company) and 2-nitrobenzyl perfluorooctanoate (Compound 1) at various weight percentages based on solids. The solutions were coated onto strips of copper foil using a #8 wire wound coating rod (R.D. Specialties Company). The coated samples (coating thickness was about 20 μm) were allowed to air dry one hour. A portion of each sample was irradiated with a General Electric H3T7 medium pressure mercury lamp for the times and at the distances noted in Table I. The irradiated samples were laminated with "Scotch" Brand "Magic Mending" Tape (available from the 3M Company) and the tape then peeled at a 180° angle from the sample. The mode of adhesive failure for each was observed and indicated in Table I.

It is apparent from the data in Table I that carboxy functionalized acrylic resin containing from more than 1% to less than 10% of photolabile blocked surfactant (Compound 1) adheres well to copper foil until it has been irradiated, whereon it is readily removed from the copper foil.

TABLE I

| Ex. No. | Compound 1 | Radiation (Time/Distance) | Peel Result[(a)] |
|---|---|---|---|
| 13 | 1.0 | 0 min | NR |
| 13 | 1.0 | 9 min/2.5 cm | NR |
| 13 | 1.0 | 20 min/10 cm | NR |
| 14 | 2.0 | 0 min | NR |
| 14 | 2.0 | 3 min/2.5 cm | R |
| 14 | 2.0 | 15 min/10 cm | R |
| 15 | 5.0 | 0 min | NR |
| 15 | 5.0 | 2 min/2.5 cm | R |
| 15 | 5.0 | 10 min/10 cm | R |
| 16 | 10.0 | 0 min | R |

[(a)]"R" indicates that release of the coating from the substrate copper occured and "NR" indicates that release of the coating from the substrate did not occur. In other tables "R/NR" indicates that there was only partialrelease of the coating from the substrate.

EXAMPLES 17-22

Examples 17-22 illustrate the inoperability of photolabile blocked compounds that are not sufficiently surfactant.

Samples of "Carboset" 525[2.] (20% methylethylketone) containing 5 and 10 weight percent of 2-nitrobenzyl trifluoro-acetate based on total solids were coated with a #50 coating rod onto Parker "Bonderite" #40[3.] steel panels. Portions of the dried, coated samples were irradiated with the GE H3T7 lamp for up to 30 minutes at 5 cm distance. Pressure sensitive adhesive tape (#610 available from the 3M Company) was applied to each portion and peeled off at a 180° angle. The resin-metal adhesion showed failure at the tape-resin interface. No photorelease was observed. The identical result (no photorelease) was obtained when the perfluorobutanoate and perfluorohexanoate esters of 2-nitrobenzyl alcohol were used in place of 2-nitrobenzyl trifluoroacetate.

EXAMPLE 23

A solution containing 10% by weight of a high molecular weight poly(methyl methacrylate) available under the trade designation "Elvacite" 2041 from DuPont and 6% by weight of 2-nitrobenzyl perfluorooctanoate (Compound 1) based on total solids was coated onto copper foil using a #26 coating rod. The sample was dried and irradiated for three minutes with a GE H3T7 lamp at 2.5 cm. Pressure sensitive tape, laminated to the coating and peeled off, easily removed the coating from the copper foil in irradiated areas.

EXAMPLES 24-27

To a solvent solution containing 38.2% by weight of safflower alkyd modified polyurethane resin, sold under the trade designation "EPIC" varnish by the Enterprise Paint Company of Wheeling, Ill. was added sufficient 2-nitrobenzyl perfluorooctanoate to provide 5% and 10% by weight of octanoate based on total solids. Portions of the mixture were brush coated onto Parker "Bonderite" #40$^3$. steel test panels and onto copper foil strips. The coatings were allowed to dry for 16 hours. Samples were then irradiated for three minutes using the output of a GE H3T7 lamp at a distance of 2.5 cm. Pressure sensitive adhesive tape (#610 sold by the 3M Company) was laminated to each sample and peeled off at 180°. The varnish cleanly delaminated from the steel panels and copper strips in exposed areas but not in unexposed areas.

EXAMPLES 28-31

Examples 24-27 were repeated using sufficient 2-nitrobenzyl hexadecanesulfonate (Compound 9) to provide the varnish with 4% by weight of the photolabile sulfonate based on total solids. The varnish cleanly delaminated from metal strips in exposed samples but not from unexposed samples. When the examples were repeated using varnish with 5% by weight of 2-nitrobenzyl hexadecanesulfonate (Compound 9) adhesion of the coating was poor even in the absence of irradiation.

EXAMPLES 32-35

A series of coating solutions were prepared in methylethylketone to contain 20% by weight of "Carboset" 525$^2$. and α-methylphenacyl perfluorooctanoate (Compounds 2) at various weight percentages based on total solids. The solutions were coated onto Parker "Bonderite" #40$^3$. steel panels and copper foil using a #50 coating rod and air dried overnight. Samples of the coatings were irradiated as noted in Table II and the coating tested for adhesion by peeling a laminated #610 (sold by the 3M Company) pressure sensitive adhesive tape from the coating as is described in Examples 13-16.

Data presented in Table II shows that the coating compositions of "Carboset" 525$^2$. are readily photoreleased from copper substrates when there is present about 2% of photolabile blocked surfactant Compound 2 and from steel when there is present about 3% of Compound 2.

TABLE II

| Ex. No. | % Compound 2 | Radiation (Min. at 2.5 cm) | Peel Results[b] On Steel | On Copper |
|---|---|---|---|---|
| 32 | 1.0 | 0 | NR | |
| 32 | 1.0 | 1 | NR | |
| 32 | 1.0 | 3 | NR | |
| 32 | 1.0 | 7 | NR | |
| 32 | 1.0 | 10 | NR | |
| 33 | 2.0 | 0 | NR | |
| 33 | 2.0 | 1 | NR | |
| 33 | 2.0 | 2 | NR | R |
| 33 | 2.0 | 3 | NR | |
| 34 | 3.0 | 0 | NR | |
| 34 | 3.0 | 1 | R/NR | |
| 34 | 3.0 | 2 | R | R |
| 34 | 3.0 | 3 | R | |
| 35 | 5.0 | 0 | NR | |
| 35 | 5.0 | 0.25 | R/NR | |
| 35 | 5.0 | 0.5 | R | |
| 35 | 5.0 | 1 | R | R |

[b]R and NR are defined in footnote to Table I

EXAMPLES 36-40

Examples 32-35 were repeated using in place of Compound 2 as photolabile blocked surfactant the tetradeca-, hexadeca-, heptadeca-, octadecanoate and 9-octadecenoate esters of 2-nitrobenzyl alcohol (Compounds 5, 6, 7, 4 and 8, respectively). Compound 5 did not provide photorelease. Compounds 6, 7, 4 and 8 provided photorelease of coatings at concentrations above about 3% by weight in "Carboset" 525$^2$. At concentrations above about 10%, release occurred without irradiation for Compounds 6, 7, 4 and 8.

EXAMPLE 41

A coating was prepared as described in Examples 32-35 to contain 5% by weight of N-(2-nitrobenzyl)octadecylamine (Compound 23) in "Carboset" 525$^2$. After irradiation of the coating for three minutes at a distance of 2.5 cm from a GE H3T7 lamp, the coating was readily peeled from steel by #610 adhesive tape (sold by the 3M Company).

EXAMPLE 42

A solution of poly(90/10:isooctyl acrylate/acrylic acid) pressure sensitive adhesive (30% in heptane-isopropanol) was mixed with enough 2-nitrobenzyl heptadecanoate (Compound 7) to form a solution having 5% by weight of the heptadecanoate ester in the adhesive solids. The adhesive was knife coated at 50 μm orifice onto 50 μm polyester film and allowed to air dry. The sample was cut into strips and laminated onto Parker "Bonderite" #40$^3$. steel panels. Portions of the laminated construction were irradiated for five minutes at a distance of 2.5 cm from a GE H3T7 lamp. When the polyester strips were peeled at a 180° angle, the adhesive was cleanly removed along with the polyester from the steel panel in irradiated areas. In the unirradiated areas, adhesive adhered to the metal panel. In the absence of the heptadecanoate additive, adhesive adhered to the steel surface and transfered to the steel surface in both irradiated and unirradiated areas.

A sample of the above adhesive coated polyester was laminated onto aluminum which had been anodized and silicated. A six minute irradiation with a GE H3T7 lamp at 2.5 cm was enough to allow the polyester film and adhesive to be cleanly removed from the irradiated areas. In unirradiated areas of the sample, adhesive adhered to the aluminum panel on peeling off the polyester film.

EXAMPLE 43

Samples of aluminum which had been anodized and silicated were coated with 20% by weight solution in methylethylketone of "Carboset" 525[2]. containing 5% and 10% by weight based on solids of 2-nitrobenzyl perfluorooctanoate (Compound 1) and dried. The coatings adhered firmly to the aluminum, however, after irradiation at a distance of 2.5 cm from a GE H3T7 lamp for five minutes of the coating containing 5% Compound 1 and three minutes of the coating containing 10% Compound 1, the coating was easily removed by peeling off a pressure sensitive tape that had been pressed onto the coatings.

EXAMPLE 44

Carboset" 525[2]. coatings containing 3% by weight of N-octadecanoyl-8-nitro-1,2,3,4-tetrahydroquinoline (Compound 21) on "Bonderite" #40[3]. steel panels were prepared as described in Examples 32-35. The coatings could not be removed by peeling a pressure sensitive tape laminated to their surfaces. After irradiation for three minutes at a distance of 2.5 cm from a GE H3T7 lamp, the coating was easily removed by peeling off a pressure sensitive tape that had been pressed onto the coatings.

EXAMPLES 45-48

To separate portions of a 25% by weight solution of poly(90/10 isooctyl acrylate/acrylic acid) pressure sensitive adhesive in heptane-isopropanol was added sufficient 2-nitrobenzyl octadecanoate (Compound 4), 2-nitrobenzyl perfluorooctanoate (Compound 1), and 2-nitrobenzyl hexadecanesulfonate (Compound 9) to provide compositions containing 5% to 10% by weight based on total solids of each. Each solution was knife coated onto cellulose acetate film (100 μthickness) at an orifice of 75 μm and allowed to dry three hours. The adhesive coated films were then cut into 1.25 cm strips and laminated adhesive-side down to "Bonderite" #40[3]. steel panels and to anodized silicated aluminum. Strong bonding was assured by placing the samples under 1 kg weights for about 16 hours. Samples of each were exposed to the radiation from a GE H3T7 lamp at a distance of 5 cm for the times shown in Table III and the tapes peeled from the metal substrates.

Data presented in Table III shows that pressure sensitive adhesives containing a photolabile blocked surfactant of the invention are readily releasable from steel or aluminum after illumination by ultraviolet light, but are not without the illuminatiion. Blocked surfactant Compounds 4 and 9 provide ready release of adhesives from steel and aluminum at concentrations of from 5% or less to 10% or more. Blocked surfactant Compound 1 was effective on steel at concentrations of 5% or less; but on aluminum, more than 5% was needed to provide release on irradiation.

TABLE III

| Ex. No. | Compound No. | % Conc. | Radiation (Min. at 5 cm) | Peel Results[c] On Steel | On Alum. |
|---|---|---|---|---|---|
| 45 | — | — | 0 | NR | NR |
| 45 | — | — | 5 | NR | NR |
| 45c | — | — | 10 | NR | NR |
| 46a | 4 | 5 | 0 | NR | NR |
| 46 | 4 | 5 | 5 | R/NR | NR |
| 46 | 4 | 5 | 10 | R | R/NR |

TABLE III-continued

| Ex. No. | Compound No. | % Conc. | Radiation (Min. at 5 cm) | Peel Results[c] On Steel | On Alum. |
|---|---|---|---|---|---|
| 46 | 4 | 10 | 0 | NR | NR |
| 46 | 4 | 10 | 5 | R | R |
| 46 | 8 | 10 | 10 | R | R |
| 47 | 1 | 5 | 0 | NR | NR |
| 47 | 1 | 5 | 5 | R/NR | NR |
| 47 | 1 | 5 | 10 | R | NR |
| 47 | 1 | 10 | 0 | R/NR | NR |
| 47 | 1 | 10 | 5 | R | NR |
| 47 | 1 | 10 | 10 | R | R/NR |
| 48 | 9 | 5 | 0 | NR | NR[e] |
| 48 | 9 | 5 | 5 | R | R[e] |
| 48 | 9 | 5 | 10 | R | R[e] |
| 48 | 9 | 10 | phase separation[d] | | |

[c]R, N and R/NR are defined in (a) following Table I.
[d]Compound 9 is not soluble in the adhesive at this concentration
[e]Similar results are obtained when Ex. 48 was repeated using, in place of isooctyl acrylate/acrylic acid, the adhesive 90/10-(2-methylbutyl acrylate/acrylic acid), and, in place of aluminum, an enameled aluminum as substrate.

EXAMPLE 49

A solution of "Carboset" 525[2]. containing 5% relative weight solids of Compound 20 the bis-2-nitrobenzyl ester of "oleic acid dimer" ("EMPOL" 1010[1].), was coated with a #50 coating rod onto a "Bonderite" #40[3]. steel panel and allowed to dry overnight. The panel was irradiated for five minutes at 2.5 cm with a GE H3T7 lamp. The carboset film easily delaminated from the steel panel in the irradiated areas, yet held fast to the steel in the unexposed portion of the panel.

EXAMPLE 50

A solution of "Elvacite" 2044[7]. containing 3% relative weight solids of N-octadecyl-O-(2-nitrobenzyl)carbamate (Compound 19) in methlethylketone was coated onto a "Bonderite" #40[3]. steel panel and allowed to air dry. After five minutes irradiation of the film at 2.5 cm distance from a GE H3T7 lamp, the "Elvacite" film was easily delaminated from the surface of the steel panel in the exposed areas.

EXAMPLES 51-52

To solutions, one containing 20% "Carboset" 525[2]. in methylethylketone and 0.5% relative of solids of 2-nitrobenzyl hexadecanesulfonate (Compound 9), and the other containing 20% "Elvacite" 2044[7]. in methylethylketone and 1.5% relative weight solids of N-octadecyl-O-(2-nitrobenzyl)carbamate (Compound 19), where each repetitively coated onto two "Bonderite" 40[3]. steel panels to give coatings about 0.25 mm dry thickness. After five minutes irradiation at 2.5 cm distance from a GE H3T7 lamp, the films were easily stripped from the steel panel by grasping an edge of the film and peeling.

EXAMPLE 53

An adhesive tape was prepared from a 90/10 isooctylacrylate/acrylamide adhesive in ethylacetatetoluene containing 8% relative weight solids of 2-nitrobenzyl hexadecanesulfonate (Compound 9) by knife coating an adhesive solution onto polyester film. The dried tape was laminated onto a polyester film that had been primed with a coating of aluminum oxide. A portion of the tape was irradiated with a GE H3T7 lamp for five minutes at 2.5 cm. The peel strength of the tape was roughly measured with a spring scale at 180° peel angle to compare irradiated with unirradiated laminates. Peel adhesion of irradiated tapes using a peel rate of about 3.5 cm/sec was about 0 g/1.25 cm; peel adhesion of unirradiated tapes was about 425 g/1.25 cm accompanied by some adhesive transfer to the aluminum oxide surface.

EXAMPLES 54–58

Samples of "Carboset" 525[2]. (20% in methylethylketone) containing 5% and 10% relative weight solids of 3'-methoxybenzoin octadecanoate (Compound 13) were coated onto a "Bonderite" #40[3]. steel panel with a #40 coating rod. The dried samples were irradiated for the noted times with a GE H3T7 lamp at 2.5 cm and were tested for photorelease of the "Carboset" 525[2]. film.

TABLE IV

| Ex. No. | % Compound 13 | Radiation (Min. at 2.5 cm) | Peel Results[1] on Steel |
|---|---|---|---|
| 54 | 5 | 0 | NR |
| 55 | 5 | ≦20 | NR |
| 56 | 10 | 0 | NR |
| 57 | 10 | 2.5 | NR |
| 58 | 10 | 5 | R |

[1]R and NR are defined in (a) following Table I.

EXAMPLES 56–63

Samples of "Carboset" 525[2]. (20% methylethylketone) containing the concentrations based on solids of 3'-methoxybenzoin perfluorooctanoate (Compound 15) and hexadecanesulfonate (Compound 14) indicated in Table V were coated onto "Bonderite" #40[3]. steel test panels with a #40 coating rod and allowed to air dry one hour. The samples were irradiated with a GE H3T7 lamp at 5 cm for the times noted and then examined for photorelease of the "Carboset" 525[2]. film from the test panel.

TABLE V

| Ex. No. | Compound No. | % | Radiation (Min. at 5 cm) | Peel Results[1] on Steel |
|---|---|---|---|---|
| 59a | 15 | 1 | 0 | NR |
| 59b | 15 | 1 | ≦5 | NR |
| 60a | 15 | 3 | 0 | NR |
| 60b | 15 | 3 | 3 | R |
| 61 | 15 | 5 | 0 | R |
| 62a | 14 | 1 | 0 | NR |
| 62b | 14 | 1 | 1 | NR |
| 62c | 14 | 1 | 3 | R |
| 63a | 14 | 5 | 0 | R |

[1]R and NR are defined in (a) following Table I.

EXAMPLES 64–68

Adhesive tape constructions were prepared from 90/10 iso-octylacrylate/acrylic acid adhesive solution (heptane-isopropanol) containing 3% and 5% relative weight solids of 3'-methoxybenzoin hexadecanesulfonate (Compound 14). The solutions were knife coated at a 50 μm orifice onto 75 μm polyester film. The samples were air dried one hour, cut into one inch strips and laminated with heat and rubber roller pressure onto anodized-silicated aluminum. Samples of each were irradiated five minutes at 5 cm distance from a GE H3T7 lamp. The peel adhesion of unirradiated and irradiated samples were measured with a spring scale. At both concentrations, the peel force dropped from about 595 g/1.25 cm for the unirradiated samples to about 155 g/1.25 cm for the irradiated samples.

EXAMPLES 69–70

Adhesive tape constructions were prepared as follows: [69] 4.0 g of a 90/10 iso-octylacrylate/acrylic acid adhesive (25% in heptane-isopropanol) were mixed with 0.03 g 2-nitrobenzyl hexadecanesulfonate (Compound 9) in 4.0 g of methylethylketone, and [70] 4.0 g of a 95/5 isooctylacrylate/acrylic acid adhesive (25% in heptaneisopropanol) were mixed with 0.03 g 2-nitrobenzyl hexadecanesulfonate in 4.0 g of methylethylketone. The solutions were coated with a #18 coating rod onto polycarbodiimide primed polypropylene film. The samples were air dried overnight and cut into 1.25 cm strips. The strips were pressure laminated with four passes from a rubber roller onto anodized-silicated aluminum sheet. The samples were exposed to the radiation from a GE H3T7 lamp at a distance of 5 cm for the times indicated in Table VI. The force required to peel each tape sample from the aluminum was measured using a peel rate of about 3.5 cm/sec.

TABLE VI

| Radiation (Min. at 5 cm) | Peel Force | |
|---|---|---|
| | Ex. 69 (g/1.25 cm) | Ex. 70 (g/1.25 cm) |
| 0 | 1930 | 2150 |
| 0.5 | 1080 | 170 |
| 1 | 850 | 110 |
| 2 | 450 | 140 |
| 3 | 450 | 85 |

EXAMPLE 71

Super-calendered, semi-bleached 62 lb, Kraft paper (available from Thilmany Company) was coated using a #26 coating rod with: (a) 20% solution in methylethylketone of "Carboset" 525[2]. containing 1.5% by weight of 2-nitrobenzyl hexadecanesulfonate (Compound 9), (b) 10% solution in methylethylketone of "Carboset" 525[2]. containing 3% Compound 9, (c) 10% solution in methylethylketone of "Estane" 5715[8]. containing 2% Compound 9, and (d) 10% solution in methylethylketone of "Elvacite" 2044[7]. containing 5% Compound 9. Each coating was dried and exposed for three to five minutes to the radiation from a GE H3T7 lamp at a distance of 2.5 cm. The coated samples were then laminated with #610 pressure sensitive tape (sold by the 3M Company) and the tape peeled off at a 180° angle. In irradiated areas, the resin coating was cleanly removed from the paper but remained adhered to the sized paper in unexposed areas.

EXAMPLES 72–74

A sample of a 90/10 2-methylbutylacrylate/acrylic acid (14 g of a 25% solution in acetone-heptane) adhesive solution containing 0.07 g of 4,5-dimethoxy-2-nitrobenzyl hexadecanesulfonate (Compound 10) was knife coated at a 375 μm orifice onto 25 μm polyester film. The sample was allowed to air dry and was cut into strips which were laminated onto anodized aluminum, epoxy printed circuit board material, and glass slides with a hand roller. The samples were half-covered and irradiated with a GE H3T7 lamp at 10 cm for five minutes. The strips were peeled from the substrate and the mode of adhesive failure noted: R=photorelease or clean removal of adhesive from the substrate;

NR=adhesive transfer from the polyester film to the substrate.

TABLE VII

| Substrate | Irradiation Time (Min. at 10 cm) | Peel Results[1] |
|---|---|---|
| Al | 0 | NR |
| Al | 5 | R |
| Epoxy | 0 | NR |
| Epoxy | 5 | R |
| Glass | 0 | NR |
| Glass | 5 | R |

[1] R and NR are defined in (a) following Table I

Similar results are obtained when 4,5-methylenedioxy-2-nitrobenzyl hexadecanesulfonate is substituted for Compound 10. When a 90/10 iso-octylacrylate/acrylic acid adhesive is used in place of 2-methylbutyl acrylate/acrylic acid adhesive, similar results were obtained for the glass slide and aluminum substrates; however, little photorelease effect was observed for the epoxy substrate.

EXAMPLE 75

A solution of "Carboset" 525[2]. (20in methylethylketone) containing 3% relative weight solids of 4,5-dimethoxy-2-nitrobenzyl hexadecanesulfonate (Compound 10) was coated onto a sample of a gold vapor deposited layer on polyester film with a #26 coating rod. The dried sample was irradiated with a Beskey Ascor 2 kw photopolymer medium pressure mercury bulb through glass at 45 cm for three minutes. In the irradiated areas, the "Carboset" 525[2]. film could easily be peeled from the gold surface. In the unexposed areas, the "Carboset" 525[2]. film remained tightly adhere to the gold layer.

EXAMPLE 76

A sample of 15 g of a 15% solution of "Vinac" ASB 516[9]. (Air Products Company vinylacetate resin) in methylethylketone and a solution of 0.07 g of 4,5-dimethoxy-2-nitrobenzyl hexadecanesulfonate (Compound 10) in 0.2 ml of methylene chloride were mixed and knife coated at a 75 μm orifice onto a sample of vapor coated aluminum (500 Å thick) on 75 μm polyester. The sample was allowed to air dry 30 minutes and was irradiated with a Beskey Ascor 2 kw photopolymer lamp at 45 cm through glass for 90 seconds. In the irradiated areas the "VINAC" film[9]. was cleanly removed from the aluminum surface. In unirradiated samples, the "VINAC" film[9]. adhered tightly to the aluminum.

An identical result was obtained when a polyester resin, Goodyear "Vitel" PE-222[10]. (15% in methylethylketone), was substituted for the "VINAC" ASB 516[9]. resin. The "Vitel"[10]. resin could also be made to photorelease from the surface of vapor coated nickel on polyester using the above procedure and three minutes of irradiation.

EXAMPLE 77

A sample of "Vitel" PE-222[10]. resin (15% in methylethylketone) containing 3% relative weight solids of 4,5-dimethoxy-2-nitrobenzyl hexadecanesulfonate (Compound 10) was coated with a #38 coating rod onto 75 μm polyester film which had been primed by exposure to a corona discharge. The dried sample was irradiated for three minutes with a Beskey Ascor 2 kw photopolymer lamp at 45 cm. The irradiated "Vitel" resin was easily peeled from the corona primed polyester film. Unirradiated areas adhered tightly. When the procedure was repeated for unprimed samples of polyester film, the "Vitel"[10]. resin adhered tightly in both irradiated and unirradiated areas.

EXAMPLE 78

Preparation of β-Nitrocinnamyl Alcohol

Benzaldehyde (10.6 g, 0.1 mol) and 2-nitroethanol (9.1 g, 0.1 mol) were dissolved in 25 ml of methanol. The mixture was cooled in an ice bath and 10 ml of 10.5M aqueous sodium hydroxide was added dropwise with stirring at such a rate that the temperature of the reaction was maintained below 15° C. As the addition progressed a white precipitate separated. Water (70 ml) was added 15 minutes after completion of the addition and the reaction was poured into 50 ml of 4.8M hydrochloric acid. The oil product was separated from the aqueous (upper) layer by decanting and the product was taken up in ether. The ether solution was washed three times with sodium bisulfite solution to remove any unreacted benzaldehyde. The ether layer was dried and evaporated in vacuo to yield the product as an oil.

EXAMPLE 70

Preparation of β-Nitrocinnamyl Perfluorooctanoate

β-Nitrocinnamyl alcohol (5.4 g, 0.03 mol) and one equivalent of triethylamine (3.03 g, 0.03 mol) were dissolved in 100 ml of toluene. The solution was cooled in an ice bath and perfluorooctanoyl chloride (12.6 g, 0.03 mol) was added dropwise with stirring. The reaction was stirred an additional two hours and diluted with ether. The reaction was extracted with water and the organic layer was dried over anhydrous magnesium sulfate and evaporated in vacuo. The only product was crystallized from petroleum ether to give yellow prisms, mp 79°–81°, IR 1785, 1655, 1535, 1325, and 1200 cm$^{-1}$. A solution of the material in 95% ethanol showed an absorption of $\lambda_{max}$ at 302 nm, epsilon=10,800 which rapidly decreased on exposure to the GE H3T7 source. This loss of the 302 nm absorption was accompanied by a decrease in the pH (increased acidity) of the solution as as indicated by methyl red pH indicator.

EXAMPLE 80

β-Nitrocinnamyl perfluorooctanoate as a photolabile blocked surfactant

A sample of 0.01 g of β-nitrocinnamyl perfluorooctanoate was dissolved in a 20% solution of "Carboset" 525[2] in methylethylketone. The mixture was coated onto a "Bonderite"[3] #40 steel panel with a #8 coating rod. The air dried sample (overnight at 20° C.) was partially covered and irradiated with a GE H3T7 source at a distance of 5 cm for 5 minutes. Adhesive tape (#610 available from the 3M Company) was applied to the scored resin surface and peeled. The resin released from the metal surface only in the exposed area.

Footnotes

1. "EMPOL" 1010 is the trade designation of Emery Industries, Inc. for 9-octadecenoic acid dimer.
2. "Carboset" 525 is the trade designation of the B.F. Goodrich Company for a carboxy functionalized acrylic resin.
3. "Bonderite" #40 is the trade designation of the Oxy-Metal Industries Corporation, Parker Division for a phosphate surface treatment for unpolished cold rolled steel test panels.
4. "Elvacite" 2041 is the trade designation of the DuPont Company for a high molecular weight poly(methyl methacrylate).

5. "EPIC" varnish is the trade designation of the Enterprise Paint Company of Wheeling, Ill. for a solvent solution containing 38.2% by weight of safflower alkyd modified polyurethane resin.
6. "Styron" 678 is the trade designation of the Dow Chemical Company for a general purpose polystyrene.
7. "Elvacite" 2044 is the trade designation of the DuPont Company for medium molecular weight poly(n-butylmethacrylate).
8. "Estane" 5715 is the trade designation of the B.F. Goodrich Company for a polyurethane elastomer.
9. "VINAC" ABS 516 is the trade designation of the Air Products Company for a vinylacetate resin.
10. "Vitel" PE-222 is the trade designation of the Goodyear Tire and Rubber Company for a linear saturated polyester resin.

What is claimed is:

1. A photolabile blocked surfactant compound having the general formula $(P-X)_a R$ wherein
   $(-X)_a R$ is the hydrogen-eliminated residue of a surfactant having the formula $(H-X)_a R$ wherein X is a polar divalent radial wherein X is $$-\underset{R^1}{\underset{|}{N}}-$$

wherein $R^1$ is hydrogen or lower alkyl having from 1 to 4 carbon atoms;
   P is a photolabile masking group which prior to exposure to actinic radiation masks the polar properties of X and upon exposure to actinic radiation will unmask the polar properties of X;
   R is a hydrophobic group which provides in said surfactant $(H-X)_a R$ a log (critical micelle concentration) equal to or less than -2 and is selected from:

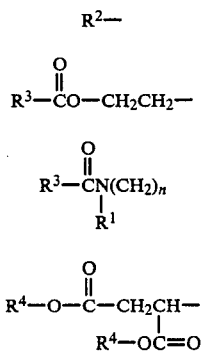

wherein $R^2$ is
   (1) straight chain alkyl, alkenyl, alkynyl, or alkylphenyl group having 15 to 30 carbon atoms; or
   (2) a perfluoroalkyl, -alkenyl, or -alkynyl group having 7 to 30 carbon atoms;
   $R^3$ is a straight chain alkyl, alkenyl, alkynyl, or alkylphenyl group having 11 to 30 carbon atoms or a perfluoroalkyl group having 7 to 30 carbon atoms;
   $R^4$ is a straight chain alkyl, alkenyl, alkynyl, alkylphenyl or perfluoroalkyl, -alkenyl, or -alkynyl group having 7 to 30 carbon atoms; and
   n is 1 or 2; and
   a is a number from 1 to 4 to satisfy the valency of R.

2. The photolabile blocked surfactant compound of claim 1 having a general formula selected from the group consisting of

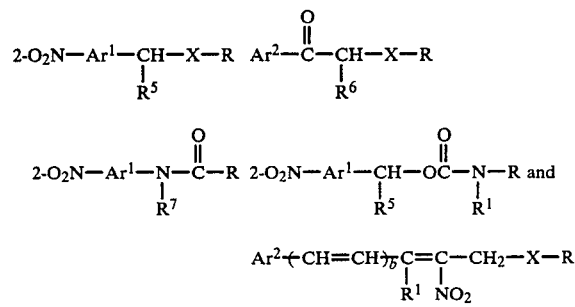

wherein:
   $Ar^1$ is a mononuclear or polynuclear divalent aryl group having 6 to 14 carbon atoms or heteroaromatic group having 5 to 13 carbon atoms with heteroatoms selected from oxygen, nitrogen or sulfur atoms, the nuclei of which may be substituted by one auxochromic or bathochromic group;
   $Ar^2$ is the same as $Ar^1$ except that $Ar^2$ is monovalent;
   $R^5$ is hydrogen, lower alkyl, phenyl, phenyl substituted by an auxochromic or bathochromic group as defined for $Ar^1$, or a lower alkylene group joining CH to $Ar^1$ and forming a five- or six-membered heterocyclic ring;
   $R^6$ is phenyl substituted by 3-alkoxy or 3,5-dialkoxy in which the alkyl group can be a hydrogen atom, a lower alkyl group, having from 1-4 carbon atoms, or a phenyl group;
   $R^7$ is hydrogen, lower alkyl having from 1-4 carbon atoms, or lower alkylene having 2-carbon atoms joining N to $Ar^2$ forming a 5- or 6-membered heterocyclic ring; and
   b is zero or one.

* * * * *

UNITED STATES PATENT AND TRADEMARK OFFICE
CERTIFICATE OF CORRECTION

PATENT NO. : 4,740,600
DATED     : April 26, 1988
INVENTOR(S) : Eian et al

It is certified that error appears in the above-identified patent and that said Letters Patent is hereby corrected as shown below:

Column 3, line 57, delete "or".

Column 5, line 54, before "N-Octadecyl-O-(2-nitrobenzyl)-carbamate" insert --N-Hexadecyl-O-(2-nitrobenzyl)carbamate-- as a new and separate line.

Column 12, line 54, delete "partialrelease" and insert in its place --partial release--.

Signed and Sealed this

Twenty-third Day of May, 1989

Attest:

DONALD J. QUIGG

Attesting Officer

Commissioner of Patents and Trademarks